United States Patent [19]
Baron et al.

[11] Patent Number: 5,106,745
[45] Date of Patent: Apr. 21, 1992

[54] BROAD SPECTRUM VIRUS INHIBITOR, UTI-β

[75] Inventors: Samuel Baron; Dorian H. Coppenhaver; Indra P. Singh, all of Galveston, Tex.

[73] Assignee: Board of Regents, The University of Texas System, Austin, Tex.

[21] Appl. No.: 446,630

[22] Filed: Dec. 6, 1989

[51] Int. Cl.⁵ ..................... A61K 37/10; C12N 5/00
[52] U.S. Cl. ................................. 435/240.2; 514/8; 514/2; 530/350; 530/395; 530/380
[58] Field of Search ............... 514/8, 2, 21; 530/350, 530/395, 380; 435/4, 240.2

[56] References Cited

FOREIGN PATENT DOCUMENTS 2117385A 10/1983 United Kingdom .

OTHER PUBLICATIONS

Coppenhaver et al., "Size and Stability of a Naturally Occurring Virus Inhibitor", Antimicrobial Agents and Chemotherapy, 25:646–649 (1984).

Kumar et al., "A Broadly Active Viral Inhibitor in Human and Animal Organ Extracts and Body Fluids (41918)", Proc. Soc. Exp. Bio. and Med., 177:104–111 (1984).

Baron et al., "A New Subtype of a Natural Viral Inhibitor (CVI) that is Stable in the Gastrointestinal Tract", Microbial Pathogenesis, 1:241–247 (1986).

Baron et al., "Recently Described Innate Broad Spectrum Virus Inhibitors", Microbial Pathogenesis, 7:237–247 (1989).

Primary Examiner—F. T. Moezie
Attorney, Agent, or Firm—Arnold, White & Durkee

[57] ABSTRACT

A broadly active viral inhibitor, termed UTI-β, is disclosed and having the following characteristics:

(a) an apparent molecular mass of about 60 to about 90 kDa, based on HPLC size exclusion chromatography;
(b) broad antiviral activity against a number of different viruses including herpesviruses, poxviruses, picornaviruses, paramyxoviruses, alphaviruses, flaviviruses and bunyaviruses;
(c) lacking species specificity;
(d) stable to temperatures ranging between 4° C. and 80° C., and denatured by treatment at 80° C. for greater than 10 minutes;
(e) unstable to periodate oxidation;
(f) found spontaneously in mammalian host serum in the absence of viral infection;
(g) both carbohydrate and protein structure; and
(h) stable or enhanced viral inhibitory activity after proteolytic digestion.

This viral inhibitor is useful for the treatment and prophylaxis of a broad range of viral infections occurring in mammalian hosts.

6 Claims, No Drawings ated States Patent Number 5,106,745

BROAD SPECTRUM VIRUS INHIBITOR, UTI-β

FIELD OF THE INVENTION

This invention relates to the isolation and characterization of viral inhibitor substances naturally produced by mammals.

BACKGROUND OF THE INVENTION

A number of viral inhibitors occur in the body. Some inhibitors, including antibodies and interferons, are induced as a consequence of viral infection. Other inhibitors spontaneously occur in the uninfected host. They range from narrow to broad antiviral activity and inhibit viruses by diverse mechanisms.

In recent years, we studied three broadly active viral inhibitors that are produced spontaneously in the body or in cell culture. We tentatively have named them (a) contact-blocking viral inhibitor (CVI), (b) UTI-α, and (c) UTI-β. These naturally produced inhibitors may serve as host defenses against a number of virus groups.

The three inhibitors, CVI, UTI-α and UTI-β, share one major characteristic: broad antiviral activity. The distinguishing features of these three inhibitors are their molecular size, essential chemical composition, thermal and chemical stability, and physiologic site of occurrence.

CVI was first detected unexpectedly during characterization of interferon preparations from tissue culture. The interferon preparations under study contained a second inhibitor (CVI) with properties that clearly differentiated it from interferon. Some of these properties not only distinguish this inhibitor from other previously reported inhibitors but also had surprising molecular properties. The distinguishing properties of CVI include: inhibition of attachment of many viruses to cells; apparent molecular size of 3000–4000 kDa; essential peptide and carbohydrate structure; high stability to physical and chemical agents; reversibility of inhibition; and production in a number of cell cultures.

UTI-α was discovered unexpectedly when we surveyed body fluids and tissue extracts for CVI which we had found previously in cell cultures. Many body fluids and tissue extracts contained a broadly active viral inhibitor but with properties clearly distinct from those of CVI. Those properties which distinguished UTI-α from CVI are: inhibiting of replication of some viruses (as well as viral attachment for most viruses); molecular size between 500 and 3000 daltons; essential carbohydrate structure; extreme thermal stability; and presence in many body fluids and tissue extracts.

UTI-β was recently discovered in human sera when it was found that the broad spectrum antiviral activity in normal human serum was distinct from CVI and from UTI-α.

Other virus inhibitors have been reported from human serum. These include inhibitors of myxoviruses (alpha or Francis, beta or Chu, gamma, and C), inhibitors of influenza, NDV, and mumps (Krizanova et al., "Serum Inhibitors of Myxoviruses," *Curr. Top Microbiol. Immunol.* 47:125 (1969) and Karzon, "Nonspecific Viral Inactivating Substance (VIS) in Human and Mammalian Sera," *J. Immunol.* 76:454–463 (1956)), poxviruses (Kitamura et al., "Studies on a Heat-Labile Variola Virus Inhibitor in Normal Sera II. Further Characterization of the Inhibitor and its Activity," *Intervirology* 1:288–296 (1973)), togaviruses (Shortridge et al., "Human Serum Lipoproteins as Inhibitors of Hamagglutination for Selected Togaviruses," *J. Gen. Virol.* 23:113–116 (1974)), coronavirus (Gerna et al., "Human Coronavirus OC-43 Serum Inhibitor and Neutralizing Antibody by a New Plaque-Reduction Assay," *Proc. Soc. Exp. Biol. Med.* 163:360–366 (1980)), Sendai virus (Suribaldi et al., "Inhibiting Activity of Human Serum Low Density Lipoprotein Toward Sendai Virus," *Microbiologics* 2:121–128 (1979)), retroviruses (Welsh et al., "Inactivation and Lysis of Oncornaviruses by Human Serum," *Virology* 74:432–440 (1976)), and rhabdoviruses (Thiry et al., "Factors Which Influence Inactivation of Vesicular Stomatitis Virus by Fresh Human Serum," *Virology* 87:384–393 (1978)). Normal animal sera also posses a wide spectrum of viral inhibitors, many of which are homologous to those found in human sera. These inhibitors affect adeno, polio, ECHO, arbo, myxo, vaccinia, variola, Rous sarcoma, lymphocytic choriomengititis, measles, and herpes (Allen et al., "Viral Inhibitors in Normal Animal Sera," *Tex. Rep. Biol. Med.* 16:39–421 (1958)), vesicular stomatitis, encephalomyocarditis, and caprine herpes viruses (Yilma et al., "Preliminary Characterization of a Serum Viral Inhibitor," *Am. J. Vet. Res.* 46(11):2360–62 (1985)). The properties reported for these inhibitors indicate that they are from CVI, UTI-α and UTI-β.

SUMMARY OF THE INVENTION

The present invention provides a partially purified broadly active viral inhibitor, UTI-β, which spontaneously occurs in uninfected mammalian hosts. Although UTI-β shares a broad antiviral spectrum with CVI and UTI-α, it is distinguished by: molecular size of approximately 60–90 kDa; lability at 80° C.; conversion to a heat stable low molecular weight inhibitor by proteolysis; inactivation by mild oxidation (periodate) suggesting essential carbohydrate structure; and affinity for concanavalin A lectin, confirming the presence of carbohydrate moieties on the active molecule.

DETAILED DESCRIPTION OF PREFERRED EMBODIMENTS

Broadly Active Viral Inhibitor from Human Serum (UTI-β)

The present invention provides a broadly active viral inhibitor found in human serum, and provisionally termed UTI-β. UTI-β occurs in normal serum in significant titers ($\geq 64$ U/ml) and is active against a wide range of viruses in cells of different species. UTI-β differs from previously identified CVI and UTI-α in size, thermostability and chemical nature. UTIβ appears to have a native molecular size in the range of 60–90 kDa, based on HPLC size exclusion chromatography, and shows moderate heat stability, being denatured by treatment at 80° C. for greater than 10 minutes. UTI-β possesses a protein component which is not essential for antiviral activity, unlike UTI-α which is protein free, and CVI, which has essential protein structure. UTI-β shows antiviral activity against enveloped and non-enveloped RNA and enveloped DNA viruses. See TABLE I. The inhibitory activity varies with the virus used and ranges from 8 to 144 U/ml but is uniformly higher for enveloped RNA viruses. The method used to determine antiviral titers was the same as we have used previously in the study of other inhibitors. Baron et al., "Broadly Active Inhibitor of Viruses Spontaneously Produced by Many Cell Types in Culture," Infec. and Immunity 32:449-453 (1981). It is unknown whether this observation is a reflection of the mechanism of action of the inhibitor.

TABLE 1
ANTIVIRAL SPECTRUM OF THREE NATURALLY-OCCURRING INHIBITORS

| VIRUS | TYPICAL ANTIVIRAL TITER* OF INHIBITOR TYPE | | |
|---|---|---|---|
| | CVI | UTI-α | UTI-β |
| DNA Viruses | | | |
| Herpesviruses | | | |
| Herpes simplex I (HSV-I) | 6 | 18 | 32 |
| Varicella-Zoster (VZ) | — | 64 | — |
| Poxviruses | | | |
| Vaccinia | 32 | 32 | 18 |
| RNA Viruses | | | |
| Picornaviruses | | | |
| Polio | 16 | 12 | 24 |
| Mengo | — | 48 | 8 |
| Orthomyoviruses | | | |
| Influenza A | — | 128 | — |
| Paramyxoviruses | | | |
| Newcastle disease (NDV) | <2 | 24 | 96 |
| Reoviruses | | | |
| Rotavirus | — | 4 | — |
| Alphaviruses | | | |
| Semliki Forest | 8 | 8 | 64 |
| Sindbis | 30 | 48 | 96 |
| Flaviviruses | | | |
| Banzi | — | — | 64 |
| Bunyaviruses | | | |
| Bunyamwera | — | — | 144 |
| Rhabdoviruses | | | |
| Vesicular stomatitis (VSV) | 6 | 24 | — |

*Plaque reduction titer 50%, except hemagglutination yield reduction 50% for influenza A. Cells in assay varied with the virus tested. — = not tested.

Human serum also contains a smaller broadly active viral inhibitor, which passes through dialysis tubing of 12-14 kDa retention and constitutes about 10-20% of total virus inhibiting activity. (Approximately 80-90% of the non-specific antiviral activity is retained under the same conditions and represents the protein-bound antiviral activity of 60-90 kDA which we identify as UTI-β.) In light of the presence of the minor, small molecular weight serum activity (probably UTI-α; see below), we routinely remove that component before analysis of UTI-β. Thus, in all experiments summarized here characterizing UTI-β, serum was first exhaustively dialysed to remove the small molecular weight antiviral component.

The native UTI-β appears to possess both protein and carbohydrate structure. Mild oxidation with sodium metaperiodate destroys UTI-β activity, suggesting that carbohydrate structure is essential to the antiviral activity. Proteolytic digestion consistently increases the inhibitor activity about three-fold, however. About 90% of the antiviral activity of protease-digested UTI-β is associated with a newly generated 1-3 kDa component(s). These data raise several possibilities about the structure of native UTI-β. Native UTI-β could represent a polymeric or multimeric structure. Another possibility is that the small (1-3 kDa) antiviral molecules are specifically or non-specifically bound to a carrier protein in the serum. TABLE 2 summarizes the effects of proteolytic digestion of UTI-β.

TABLE 2
Alteration in the Properties of the Serum Inhibitor (UTI-β) by Proteolytic Treatment

| Properties | UTI-β | |
|---|---|---|
| | Untreated | Treated |
| Activity | 20 U | 58 U |
| Size | 60-90 kDa | 1-3 kDa |
| Thermostability | 80° for 10 min. | 120° C. for 15 min. |

Proteinase K was added in a final concentration of 0.33 mg/ml and the mixture was incubated for four hours at 37° C. by the method of Sullivan et al. (1987).* The activity was assayed by the 50% plaque reduction method of CER cells using Bunyamwera virus.

*Sullivan et al., "Characterizations of an Antiviral Agent from Primary Murine Fibroblast Cultures: Murine Tissue Culture CVI," J. Biol. Regul. Homeost. Agents 1:126-132 (1987).

The proteolytic conversion of the large size inhibitor to a smaller inhibitor with properties similar to those observed for UTI-α is suggestive evidence that UTI-α and β may be related. However, preliminary attempts to generate the small molecular weight inhibitor without breaking covalent bonds by disrupting the native structure of UTI-β by sulfhydryl or chaotropic agents did not do so. Nevertheless, these experiments do not eliminate the possibility that the naturally occurring small molecular weight inhibitor from sera is related to the protease-released form of UTI-β. It may be that native UTI-β and the small size, protease-released, activity exist in equilibrium.

The mechanism of action of UTI-β appears to be complex. The inhibitor does not bind tightly to virus particles, since infective virus can be recovered by simply diluting virus-inhibitor mixtures. One mode of action of native UTI-β is the prevention of viral attachment to cells, as judged by measuring inhibition of viral infectivity during absorption of virus onto cells at 4° C., by the method of Sullivan et al., J. Biol. Recul. Homeost. Agents I:126-132 (1987) and Kumar et al., Proc. Soc. Exp. Biol. Med. 177:104-111 (1984). Some viruses (e.g., HSV I) appear to be inhibited at a post-adsorption step, however. Preliminary experiments indicate that pretreatment of cells with native UTI-β preparations induces a durable antiviral state accounting for a significant portion of the antiviral activity against a member of the Bunyavirus family, but not the other viruses tested. It is currently unknown whether the latter represents a surface or intracellular phenomenon or whether more than one inhibitor remains in the serum preparations. The precise antiviral mechanisms of UTI-β remain to be determined, as do the roles of the native (60-90 kDa) and protease-related (<3 kDa) forms of the antiviral molecule.

Antiviral Activity from Cell Culture: Contact Blocking Viral Inhibitor (CVI)

We originally identified a broadly active, spontaneously produced viral inhibitor in supernatants from a variety of cells grown in culture (Baron et al., "Broadly Active Inhibitor of Viruses Spontaneously Produced by Many Cell Types in Culture," Infec. and Immunity 32:449-453 (1981); see also U.S. Pat. No. 4,595,588). This inhibitor, which acted primarily by blocking the attachment of virus to target cells, was named contact-blocking viral inhibitor, or CVI. CVI is produced in various primary and secondary cell lines of human and murine origin, and continuous human, mouse, sheep and rabbit cell lines. The level of antiviral activity produced varies with the cell type; titers vary 40-fold between low and high producing lines.

Primary mouse embryo fibroblast (MEF), after several passages, have been shown to consistently produce significant CVI activity (24-64 units/ml) and have been used as the source of CVI for partial purification and characterization of CVI (Sullivan et al., *J. Biol. Regul. Homeost. Agents I*:126-132 (1987) and Hughes et al., "Cell-Produced Viral Inhibitor: Possible Mechanism of Action and Chemical Composition," Infec. Immunity 32(2):454-457 (1981)).

Production of CVI is independent of cell density and subculturing protocols, except as noted above for MEF. Additionally, it is produced constitutively and rapidly with significant levels observed in culture supernatants from cell monolayers beginning within one hour of washing with fresh media. Spontaneous and continuous production is also suggested since inhibiting macromolecular synthesis by treating cells with actinomycin D or cyclohexamide blocks the appearance of the inhibitor.

As shown in TABLE 1, CVI possesses a broad but not universal antiviral activity. Significant antiviral activity is observed against representative DNA, and enveloped and non-enveloped RNA viruses (herpes and poxviruses, picorna, alpha and rhabdoviruses). The lack of significant antiviral activity against NDV is one factor which distinguishes CVI from the non-specific inhibitors (UTI-$\alpha$ and UTI-$\beta$) found in tissues and physiological fluids.

A critical difference between CVI and another broadly antiviral substance, interferon, is in the absence of species specificity of this viral inhibitor. Although the relative antiviral titer of CVI from a given source differs when assayed on various cell types, CVI has been shown to be active on all heterologous cell lines tested. Interestingly, there is no obvious correlation between the relative antiviral titer observed for a cell type with heterologous CVI and its ability to produce CVI in culture.

The mechanism of action of CVI appears to be a rapidly reversible and non-progressive extracellular inhibition of viral attachment to cell membranes. In this regard, antiviral activity is removed by washing and/or dilution and is not observed if CVI is introduced at times after viral infection of cells has occurred in single virus growth cycle experiments (Hughes et al., *Infec. Immunity* 32(2);454-457 (1981)). A mechanism involving blockage of viral attachment to cell surfaces is also indicated as antiviral activity is not reduced by incubation with virus at 4° C. (Sullivan et al., *J Biol. Regul. Homeost. Agents I*:126-132 (1987)). These properties are consistent with a substance which displays low affinity reversible binding to viral particles or cells interfering with subsequent attachment to cell surfaces.

The clinical and physical properties of CVI are summarized in TABLE 3. This antiviral activity is distinct from most other broad spectrum viral inhibitors by virtue of its large molecular size. Gel filtration chromatography and ultrafiltration experiments both suggest that the antiviral component is extremely large, with an apparent molecular weight of >200,000 daltons. Sedimentation on discontinuous sucrose gradients yields the antiviral activity at a sedimentation rate equivalent to 3000-4000 kDa. This surprisingly large size is not unprecedented; the Tamm-Horsfall glycoprotein was reported to be approximately 7000 kDa, although that urinary antiviral molecule was less heat stable than is CVI and has a narrow antiviral spectrum. The sedimented CVI exhibits the same biological properties as the unsedimented material, being active against vaccinia, polio and HSV viruses, two alphaviruses, vesicular stomatitis virus and inactive against NDV. The possibility that the antiviral activity originates from shed membrane fragments has been excluded, since (1) MEF membranes, prepared by freeze thawing and discontinuous sucrose gradients, fail to show antiviral activity; and (2) activity is not affected by extraction with lipid solvents (Sullivan et al., *J. Biol. Regul. Homeost. Agents* I:126-132 (1987)).

The physical-chemical properties of CVI are quite distinctive. CVI possesses a thermal stability intermediate between UTI-$\alpha$ and UTI-$\beta$, being stable at 100° C. for up to two hours but unstable at 120° C. The antiviral activity is unaffected by treatment with RNase, DNase or ether and butanol extraction, but is sensitive to proteolytic enzymes and mild oxidation with periodate. However, CVI is unaltered in molecular size or activity by a sulfhydryl reagent (dithiothreitol) and a protein solubilizing agent (8M urea). All these properties suggest that both carbohydrate and polypeptide components are required for the activity of native CVI. However, the structure of this antiviral with the surprising thermal and denaturation stability remains unknown. We have considered extracellular matrix components as the origin of CVI. However, studies with related compounds like heparin and carageenan show a narrow antiviral spectrum, thereby differentiating them from CVI and the other inhibitors described below.

Low Molecular Weight Inhibitor from Physiologic Fluids and Tissue Extracts (UTI-$\alpha$)

Another type of broadly active virus inhibitor is found in a variety of body secretions and tissue extracts. We have detected inhibitors with properties which match those given in TABLE 3 in bovine and human milk, mouse, rabbit and human gastrointestinal contents, and extracts of mouse, rabbit and human tissues. A similar activity, uncharacterized at present, is found in human nasal and salivary secretions and liver extracts. We provisionally refer to this material as UTI-$\alpha$. Essential characteristics which differentiate this material from the tissue culture-derived inhibitor (CVI) are its small molecular size, extreme heat stability, lack of essential peptide structure, and different antiviral spectrum (e.g., activity against NDV). Critical features which differentiate this material from the major inhibitor (UTI-$\beta$) found in human serum are its small molecular size, extreme heat stability, and lack of essential peptide structure.

Size exclusion chromatography on soft-gel and high performance liquid chromatography (HPLC) supports has consistently yielded a molecular size in the range of 500-3000 daltons for UTI-$\alpha$. The material does not contain essential peptide structure, as judged by its resistance to digestion by trypsin, chymotrypsin, and the non-specific proteolytic enzyme proteinase K. It is not extractable or inactivated by organic solvents, and shows extended stability to heat and pH denaturation. These and critical physical-chemical characteristics are summarized in TABLE 3.

TABLE 3

| Characteristics of Three Naturally-Occurring Viral Inhibitors | | | |
|---|---|---|---|
| | CVI | UTI-$\alpha$ | UTI-$\beta$ |
| Source | Tissue Culture | Tissue Fluids & Extracts | Serum |

TABLE 3-continued

Characteristics of Three Naturally-Occurring Viral Inhibitors

| | CVI | UTI-α | UTI-β |
|---|---|---|---|
| Antiviral Activity | Broad Inhibits Attachment Reversible | Broad Attachment and/or Replication Reversible | Broad Attachment and/or Replication Reversible |
| Species Specific | No | No | No |
| Thermal Stability | | | |
| 56° C. | Stable | Stable | Stable |
| 80° C. | Stable | Stable | Stable[1] |
| 100° C. | Stable | Stable | Unstable |
| 120° C. | Unstable | Stable | Unstable |
| 200° C. | Unstable | Unstable | Unstable |
| Size | 3000–4000 kDa | 0.5–3 kDa | 60–90 kDa |
| Proteolysis | Unstable | Stable | Stable |
| 8M Urea | Stable | N.D.[2] | N.D. |
| DTT | Stable | N.D. | Stable |
| Lipid Solvents | Stable (aqueous phase) | Stable (aqueous phase) | N.D. |
| Nucleases | Stable | Stable | N.D. |
| Periodate | Unstable | N.D. | Unstable |
| Possible composition | Carbohydrate-protein | Carbohydrate | Carbohydrate protein |

[1]Stable at 80° C. for only 10 minutes.
[2]N.D. = Not done

Most of our preliminary work with this low molecular weight virus inhibitor from body fluids has been done with the material from bovine milk. Hence, we are particularly careful to delineate this material from other virus-inhibitory substances that have been reported from milk. The presence of antiviral lipids in milk is well documented (Michaels, *J. Immunol.* 94:262 (1965); Fieldsteel, Cancer Res. 34:712–715 (1974); Falkler et al., *Archives of Virol.* 47:3–10 (1975); Welsh et al., *Virology* 74:432–440 (1976); Welsh et al., *Inf. and Imm.* 19(2):395–401 (1978); and Issacs et al., *J. Inf. Dis.* 154:966–971 (1986)). These materials can be differentiated from the low molecular weight inhibitor from tissues and body fluids in at least three areas:

(a) Only enveloped viruses are affected by these antiviral milk lipids, whereas UTI-α is active against both enveloped and unenveloped viruses.

(b) The mechanism of action of the milk lipid antivirals appears to be disruption of the lipid containing surface membrane of the enveloped viruses, leading to loss of the integrity of the virus particle and consequent loss of infectivity. UTI-α, in contrast, appears to function against most viruses by preventing or disrupting effective contact between the virus and target cells. It does not inactivate virus in a cell-free system. And (c) UTI-α is found in the aqueous fraction of milk, not in the lipid rich cream layer. In addition, when milk whey or gastrointestinal inhibitor (UTI-α) is extracted with organic solvents, the antiviral activity is not degraded, and remains in the aqueous phase.

A number of biological tests have been carried out to further characterize UTI-α. We have assayed inhibitor-containing preparations from human and bovine milk on cell lines of primate, rodent and avian origin. Unlike the interferons, the antiviral effect is not species specific: it is evident on all cell lines tested. However, the degree of inhibition does vary with the cell types used for assay, even when the same virus is being assayed on different cells. Also, unlike interferon, the activity does not produce a durable antiviral state in target cells, since the cells revert to susceptibility to virus attack when the inhibitor preparation is thoroughly washed off.

Preliminary studies on crude antiviral preparations from bovine milk indicate that the major antiviral effect of this inhibitor is in the prevention of attachment of the virus to the target cell, thereby preventing a productive infection from being established. This prevention of attachment was also seen for vaccinia, polio, HSV I and ND viruses. Different apparent modes of action were detected in studies of VSV, varicella zoster (VZ), influenza A and HIV, however. Our data indicate that VSV is inhibited at an early, post-penetration step in the viral infection, as judged by greater inhibition of VSV at 37° C. versus 4° C. and time of virus escape from inhibition during timed addition of inhibitor to virus infected monolayers. VZ, influenza-A, and perhaps HIV, on the other hand, all seem to be inhibited late in the replication cycle.

Although the exact structure of UTI-α has not yet been determined, there are a number of lines of evidence which are consistent with the active moiety containing carbohydrate or oligosaccharide structure. Negative evidence, summarized in TABLE 3, indicates that peptide, nucleic acid and lipid structure are not essential to the antiviral activity of this inhibitor. Chromatographic evidence obtained during the purification of the inhibitory activity is also consistent with carbohydrate structure, i.e., the inhibitory activity has slight affinity for heparin and boronate affinity HPLC columns, and is retained by a variety of lectin affinity columns. Chromatography of partially purified inhibitor from milk whey on an HPLC column optimized for separation of carbohydrates yields a >95% purification of the antiviral substance, based on recovery of activity and optical density measurements.

EXAMPLE I

Purification of UTI-β

1. Whole human serum is dialyzed against phosphate buffered saline to remove low molecular weight (less than 12,000–14,000 daltons) components.

2. Dialyzed serum is passed over a Sephacryl S-200 size exclusion column to remove high molecular weight contaminants. Active fractions are identified and pooled. Alternatively, other molecular sieving, size exclusion, or gel filtration solid phases are employed.

3. The partially purified material from step 2 is passed over a DEAE-anion exchange column maintained in 0.05M Tris-HCl at pH 7.5, and developed with a salt concentration gradient. Active fractions emerging between 0.05 and 0.075M NaCl are identified and pooled.

4. DEAE-purified active material is passed over a cibacron blue F3GA column, developed with a step gradient to 1M NaCl. Early eluting, albumin free, active fractions are identified and pooled. Alternatively, a concanavalin A lectin affinity column is used to remove all non-glycosylated components.

5. DEAE-, Cibacron Blue-, or lectin-purified active material is passed over a high performance liquid chromatography column containing C4-bonded hydrophobic stationary phase. The column is equilibrated in 0.1% trifluoroacetic acid (TFA) and developed with a linear gradient of acetonitrile containing 0.1% TFA. Organic modifier and acid are removed under $N_2$ before the fractions are assayed to determine activity. The fractions having antiviral activity are pooled and constitute UTI-β.

Utility

UTI-β is naturally present in a wide range of mammalian hosts and present throughout the body tissues and fluids, particularly serum, of those hosts. UTI-β is an antiviral agent which is spontaneously present in an uninfected host and which is not elicited in response to a specific viral challenge, yet appears to be effective in the treatment or prophylaxis of viral infection in vitro. Therefore, it is expected that by raising the in vivo titer of UTI-β normally found in a host, the resistance or elimination of viral disease can be enhanced. UTI-β would be administered to a host as a pharmaceutical composition comprising a therapeutically effective amount of UTI-β, together with a pharmaceutical carrier. Such administration to a host would include several routes, e.g., orally, intranasally, intravenously or topically.

The foregoing description of the invention has been directed to particular embodiments for purposes of explanation and illustration. It will be apparent, however, to those skilled in the art that many modifications and changes in the processes of isolating and administering the subject viral inhibitor may be made without departing from the essence of the invention as defined by the following claims.

What is claimed is:

1. An isolated viral inhibitor termed UTI-β, having the characteristics of:
   (a) an apparent molecular mass of about 60 to about 90 kDa, based on HPLC size exclusion chromatography;
   (b) broad antiviral activity against herpesviruses, poxviruses, picornaviruses, paramyxoviruses, alphaviruses, flaviviruses and bunyaviruses;
   (c) lacking species specificity;
   (d) stable to temperatures ranging between 4° C. and 80° C., and denatured by treatment at 80° C. for greater than 10 minutes;
   (e) unstable to periodate oxidation;
   (f) found spontaneously in mammalian host serum in the absence of viral infection;
   (g) both carbohydrate and protein structure; and
   (h) stable or enhanced viral inhibitory activity after proteolytic digestion.

2. An antiviral composition comprising an amount of the viral inhibitor of claim 1 effective to inhibit viral attachment to mammalian cells in vitro, together with a carrier.

3. A viral inhibitor which is a proteinase K proteolytic product of the viral inhibitor of claim 1 and which is about three times as antivirally active as the viral inhibitor of claim 1, has a molecular mass of about 1 to about 3 kDa based on HPLC size exclusion chromatography, and is stable to temperatures of about 120° C. for about 15 minutes.

4. An antiviral composition comprising an amount of the viral inhibitor of claim 3 effective to inhibit viral attachment to mammalian cells in vitro, together with a carrier.

5. An in vitro method of inhibiting the activity of a virus in mammalian cells susceptible to viral infection comprising contacting the mammalian cells with an effective amount of the viral inhibitor of claim 1, wherein said virus is herpes-virus, poxvirus, picornavirus, myxovirus, alphavirus, flavivirus or bunyavirus.

6. An in vitro method of inhibiting viral activity in mammalian cells susceptible to viral infection comprising contacting the mammalian cells with an effective amount of the viral inhibitor of claim 3, wherein said viral infection is herpes-virus, poxyvirus, picornavirus, myxovirus, alphavirus, flavivirus or bunyavirus.

* * * * *